United States Patent [19]

Ratner

[11] Patent Number: 4,965,490
[45] Date of Patent: Oct. 23, 1990

[54] SCENT-GENERATING LAMP USING MATING PARTS

[75] Inventor: Elizabeth L. Ratner, Lowell, Mass.

[73] Assignee: GTE Products Corporation, Danvers, Mass.

[21] Appl. No.: 295,091

[22] Filed: Jan. 9, 1989

[51] Int. Cl.$^5$ .......................... H01K 1/28; H01K 7/00; A62B 7/08

[52] U.S. Cl. .................... 313/569; 313/564; 313/578; 313/634; 313/315; 313/1; 422/125; 362/96; 392/386

[58] Field of Search .................... 313/1, 569, 578, 634, 313/315; 219/271, 275, 276, 538; 362/96; 422/125

[56] References Cited

U.S. PATENT DOCUMENTS

| | | | |
|---|---|---|---|
| 1,403,548 | 1/1922 | Gudeman | 422/125 |
| 1,535,486 | 4/1925 | Lundy | 219/538 |
| 1,556,680 | 10/1925 | Dorment | 422/125 |
| 1,920,599 | 8/1933 | Schuh | 167/3 |
| 2,238,476 | 4/1941 | Monteith | 299/24 |
| 2,468,164 | 4/1949 | Brewster | 219/45 |
| 2,535,802 | 12/1950 | Libson | 21/120 |
| 2,539,696 | 11/1951 | Morrison | 21/120 |
| 2,741,812 | 4/1956 | Tellier | 20/120 |
| 3,763,347 | 10/1973 | Whitaker | 219/271 |
| 3,926,655 | 12/1975 | Miles | 106/243 |
| 4,009,384 | 2/1977 | Holland | 240/108 R |
| 4,051,159 | 9/1977 | Tsoucalas et al. | 260/404.5 |
| 4,074,111 | 2/1978 | Hunter | 219/275 |
| 4,184,099 | 1/1980 | Lindauer et al. | 313/315 |
| 4,493,011 | 1/1985 | Spector | 362/96 |
| 4,544,592 | 10/1985 | Spector | 428/68 |
| 4,647,433 | 3/1987 | Spector | 422/125 |

Primary Examiner—Kenneth Wieder
Attorney, Agent, or Firm—Wolf, Greenfield & Sacks

[57] ABSTRACT

A vapor-generating electric lamp includes a sealed lamp envelop having a concave depression therein, an incandescent filament mounted within the lamp envelope, a lamp base, and a replaceable, solid insert in the concave depression. The insert produces a scent when it is warmed by heat from the filament. Preferably, the insert is a polyamide impregnated with a scent and includes a portion that matches the shape of the depression in the lamp envelope. The depression for holding the insert is preferably located at the opposite end of the lamp from the base. When the lamp is used in a base-down orientation, the insert is held in the depression by gravity.

13 Claims, 1 Drawing Sheet

SCENT-GENERATING LAMP USING MATING PARTS

FIELD OF THE INVENTION

This invention relates to electric lamps which are provided with means for generating a vapor and, more particularly, to a lamp having a depression for receiving a replaceable, solid insert which generates a scent or other vapor in response to heat from the lamp.

BACKGROUND OF THE INVENTION

Lamps having a capability for generating a vapor are well known in the art. The vapor may be a perfume or fragrance, a disinfectant, a deodorizer or any other desired vapor. Lamps in which an attachment to the lamp contains a liquid that is vaporized by heat from the lamp, are disclosed in U.S. Pat. Nos. 1,535,486 issued Apr. 28, 1925 to Lundy, 1,556,680 issued Oct. 13, 1925 to Dorment, 1,403,548 issued Jan. 17, 1922 to Gudeman and 4,074,111 issued Feb. 14, 1978 to Hunter. The Lundy patent also discloses an electric lamp having a depression that is heated with an auxiliary heating element and can contain perfumes and other scent-generating materials in fluid, paste or powder form.

Lamps having an absorbent carrier mounted around the neck of the bulb are disclosed in U.S. Pat. Nos. 1,920,599 issued Aug. 1, 1933 to Schuh, 2,468,164 issued Apr. 26, 1949 to Brewster, 2,539,696 issued Jan. 30, 1951 to Morrison, 2,741,812 issued Apr. 17, 1956 to Tellier and 2,238,476 issued Apr. 15, 1941 to Monteith. In U.S. Pat. No. 3,763,347 issued Oct. 2, 1973 to Whitaker, a lamp is coated with minute capsules containing a vaporizable material. Lamps having separate scent-generating units are disclosed in U.S. Pat. Nos. 2,535,802 issued Dec. 26, 1950 to Libson, 4,009,384 issued Feb. 22, 1977 to Holland and 4,493,011 issued Jan. 8, 1985 to Spector. Lamps having a scent-generating capsule adhered to the outer surface of the lamp envelope are disclosed in U.S. Pat. Nos. 4,544,592 issued Oct. 1, 1985 to Spector and 4,647,433 issued Mar. 3, 1987 to Spector.

A scent-generating lamp utilizing a collar formed of a polyamide resin containing perfumes or other scent generating volatile materials is disclosed in U.S. Pat. No. 4,184,099 issued Jan. 15, 1980 to Lindauer et al. polyamide resins containing volatile materials are also disclosed in U.S. Pat. Nos. 3,926,655 issued Dec. 16, 1975 to Miles and 4,051,159 issued Sept. 27, 1977 to Tsoucalás et al.

All of the known prior art scent generating lamps have had one or more disadvantages. The lamps using a liquid for producing a scent are inconvenient to use and create a risk of lamp breakage when the liquid comes into contact with a hot lamp envelope. There is also a risk of personal injury from spilled hot liquids. In some units, the scent-producing device blocks a significant portion of the light output from the lamp, while in others, the scent-producing device has a limited life and requires refilling or replacement after a short time. Many of the units have associated safety hazards and are relatively complex and expensive in construction.

It a general object of the present invention to provide improved vapor generating lamps.

It is another object of the present invention to provide scent-generating lamps that are free of safety hazards.

It is a further object of the present invention to provide scent generating lamps that produce a scent over a long period of time.

It is yet another object of the present invention to provide scent-generating lamps that are easy to use.

SUMMARY OF THE INVENTION

According to the present invention, these and other objects and advantages are achieved in a vapor-generating electric lamp comprising a sealed, light transmissive lamp envelope having a concave depression therein, an incandescent filament mounted within the lamp envelope, a base for mounting of the lamp and interconnection of the filament to a source of electrical energy, and a replaceable, solid insert in the concave depression. The insert produces a vapor such as a pleasing scent when it is warmed by heat from the filament and is of a material that can withstand the operating temperature of the lamp envelope.

Preferably, the insert is a molded polymer, such as a polyamide impregnated with a scent, and includes at least a portion that substantially matches the shape of the depression in the lamp envelope. The depression in the lamp envelope is preferably located at the opposite end of the lamp envelope from the base. When the lamp is used in a base-down orientation, the insert is held in the depression by gravity. For a base up orientation of the lamp, the insert can be held in the depression by an adhesive. In a preferred embodiment, light blockage is minimized by locating the scent-generating insert on the axis of the filament.

According to another aspect of the invention, the scent generating insert is provided with a phosphor material on its surface. Light is generated by the phosphor in a dark room.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
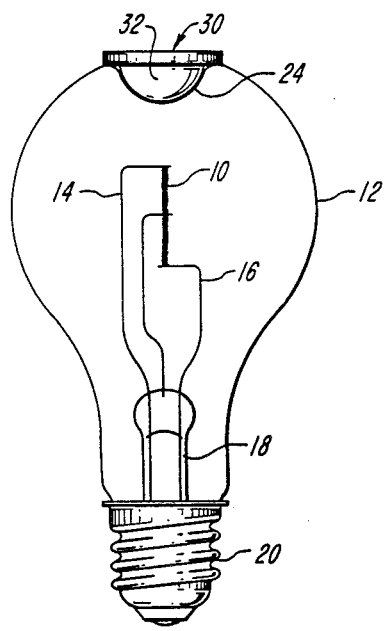
FIG. 1 is an elevational view of a scent-generating lamp in accordance with the present invention.

A scent generating lamp in accordance with the present invention is shown in FIG. 1 An incandescent filament 10 is mounted in the interior of a light-transmissive glass lamp envelope 12. The filament 10 is connected by leads 14 and 16 through a lamp stem 18 to a base 20.

A concave depression 24 is formed in lamp envelope 12 at the end of lamp envelope 12 opposite base 20. The lamp envelope 12 typically may have the same wall thickness in depression 24 as in the remainder of the lamp envelope 12. Preferably, the depression 24 is formed by molding. The glass envelope 12 is locally heated to a molten or plastic state, and a spherical graphite mold is inserted to form the contour of the depression. The diameter of the spherical graphite mold is the same as, or slightly greater than, the diameter of the convex portion of insert 30 Although the depression 24 can have any desired shape, a smoothly-curved, bowl shape is most practical. A scent-generating insert 30 is mounted in the depression 24. Although the insert 30 is a solid, it is typically a resilient material.

The insert 30 is preferably a molded polymer that can be impregnated with a perfume or other vapor-generating material. A preferred polymer is a polyamide resin blended with a perfume, fragrance essence, or other volatile material as described in the aforementioned Pat. Nos. 3,926,655, 4,051,159 and 4,184,099. A scent emanates from the polymer when the lamp is illuminated and the insert 30 reaches a sufficient temperature to cause a significant increase in the rate of migration of scent molecules through the polymer by increasing the vapor pressure of the scent in the polymer. When the lamp is not illuminated, very little scent is generated because the rate of migration of scent molecules is significantly lower. In a preferred embodiment, the insert 30 includes a convex portion 32 having a size and shape that substantially mates with the depression 24. The insert 30 is fabricated of a material that can withstand the normal operating temperature of the lamp envelope 12. In the preferred embodiment, the lamp has a 25 watt rating and the lamp envelope 12 temperature does not exceed about 120°F. When insert 30 is a polyamide resin, the melting point of the insert 30 is about 300°F.

Figure 2:
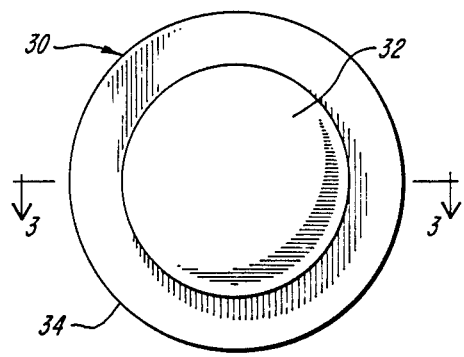
FIG. 2 is a bottom view of a scent-generating insert.
Figure 3:
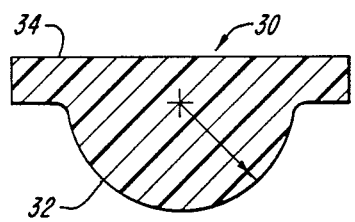
FIG. 3 is a cross-sectional view of the scent-generating insert taken along the line 3—3 of FIG. 2.

The preferred embodiment of the insert 30 is shown in FIGS. 2 and 3. The convex portion 32 has an inverted dome shape with a radius of 0.38 inch. An optional rim or flange 34 is utilized to increase the contact area between the lamp envelope 12 and the scent-generating insert 30. As the area of contact is increased, a stronger scent is generated since a greater volume of vapor is released.

When the lamp is operated in a base-down orientation, as shown in FIG. 1, the insert 30 is held in depression 24 by gravity. Since the insert 30 and the depression 24 have mating shapes, the lamp can be tipped substantially relative to vertical before the insert 30 falls out. A further advantage of the base-down orientation is that the insert 30 is located directly over the filament 10. In the case of a gas-filled lamp, maximum heat transfer from the filament 10 to the insert 30 occurs when the insert is directly over the filament, since heating of the insert in a gas filled lamp occurs primarily by convection. In a vacuum lamp, heating takes place solely by radiation. Thus, the location of a scent-generating insert on a vacuum lamp is immaterial. When the lamp is to be used in a base-up orientation, the insert 30 can be held in depression 24 by an adhesive such as a double-sided pressure-sensitive cellophane tape, such 3M Type 9485 adhesive transfer tape.

It is desired to minimize the light blockage by the insert 30. One way to minimize light blockage is by utilizing a vertical filament 10 and positioning the insert 30 on the filament axis where the light output pattern has a minimum. Light blockage is also minimized by reducing the size of the insert 30 or making it transparent.

According to another aspect of the invention, a phosphor can be added to the mixture of resin and scent-generating material so that the insert 30 glows in the dark. A preferred phosphor is an inorganic zinc sulfide phosphor, such as Hanovia GloPigment Series 1000 phosphor, which is yellow-green in color with a peak spectral response at 560 nanometers. The insert 30 thus serves two purposes: it emits a characteristic scent or fragrance when placed on an illuminated lamp, and it absorbs sufficient light energy to emit a soft glow to aid in locating it in a darkened room. The phosphor additive is non-toxic and has no characteristic odor of its own to interfere with the desired fragrance.

The scent-generating lamp of the present invention provides numerous advantages in comparison with prior art scent-generating lamps. The molded scent-generating insert 30 is completely safe and does not burn or melt, since it is fabricated of a material designed to withstand the operating temperature of the lamp envelope 12. Since the insert 30 mates with the depression 24, the insert 30 is easily positioned for use and is easily replaced when the scent is exhausted or when a different scent is desired. Furthermore, the insert 30 is retained in position by gravity without an adhesive, except for the case where the lamp is inverted or nearly inverted.

The combination of a fragrance essence with a polyamide resin as the insert material permits scent generation over long periods of time, on the order of 100 to 300 hours, before replacement of the insert 30 is required. The insert 30 does not evaporate or significantly diminish in size as the scent-generating fragrance is exhausted. A variety of different scents, deodorizers, disinfectants and the like can be used in the insert 30. The invention can be applied to lamps having different sizes, shapes and wattages, provided the insert material is selected to withstand the operating temperature of the lamp envelope.

The synergy between the lamp and its scent-generating insert arises from more than the physical matching of the two parts. The invention is designed to optimize such factors as lamp wattage, fill medium and operating temperature; the vapor pressures of the fragrance essence and the polymer insert; and the size, color and thermal characteristics of the polymer insert.

While there has been shown and described what is at present considered the preferred embodiments of the present invention, it will be obvious to those skilled in the art that various changes and modifications may be made therein without departing from the scope of the invention as defined by the appended claims.

What is claimed is:

1. A vapor-generating electric lamp comprising:
   a sealed, light-transmissive lamp envelope having a concave depression therein;
   an incandescent filament mounted within said lamp envelope;
   a base for mounting of said lamp and for interconnection of the filament to a source of electrical energy; and
   a replaceable, solid insert disposed in said concave depression, said insert producing a vapor when warmed by heat from said filament and being of a material that can withstand the operating temperature of said lamp envelope, said insert comprising only a molded polymer impregnated with a vaporizable material and including a convex portion that substantially matches said depression in shape.

2. A vapor generating electric lamp as defined in claim 1 wherein said insert comprises a molded polyamide resin impregnated with a vaporizable material.

3. A vapor-generating electric lamp as defined in claim 1 wherein said depression is located at the opposite end of said lamp envelope from said base.

4. A vapor generating electric lamp as defined in claim 1 wherein said filament has a longitudinal axis and wherein said depression is generally located on said axis.

5. A vapor generating electric lamp as defined in claim 1 wherein said insert is retained in said depression by gravity during use.

6. A vapor-generating electric lamp as defined in claim 1 further including an adhesive for retaining said insert in said depression.

7. A vapor-generating electric lamp as defined in claim 1 wherein said insert includes a rim that extends beyond the boundary of said depression for increased area of contact between said insert and said lamp envelope.

8. A vapor-generating electric lamp as defined in claim 1 wherein said lamp envelope has a substantially uniform wall thickness.

9. A vapor-generating electric lamp as defined in claim 1 further including a phosphor material disposed on the surface of said insert.

10. A vapor-generating electric lamp as defined in claim 1 wherein said lamp envelope is filled with a gas and said insert is heated primarily by convection.

11. A vapor-generating electric lamp as defined in claim 1 wherein said lamp envelope is evacuated and said insert is heated primarily by radiation.

12. A vapor-generating electric lamp as defined in claim 1 wherein the operating temperature of said lamp envelope does not exceed about 120°F.

13. A vapor-generating electric lamp comprising:
- a sealed, light-transmissive lamp envelope having a concave depression therein;
- an incandenscent filament mounted within said lamp envelope;
- a base for mounting of said lamp for interconnection of the filament to a source of electrical energy; and
- a replaceable, solid insert disposed in said concave depression, said insert producing a vapor when warmed by heat from said filament and being of a material that can withstand the operating temperature of said lamp envelope, the operating temperature of said lamp envelope not exceeding about 120°F.

* * * * *

UNITED STATES PATENT AND TRADEMARK OFFICE
CERTIFICATE OF CORRECTION

PATENT NO. : 4,965,490

DATED : October 23, 1990

INVENTOR(S) : Elizabeth L. Ratner

It is certified that error appears in the above-identified patent and that said Letters Patent is hereby corrected as shown below:

On the title page, item [75] Inventor: change "Elizabeth L. Ratner" to --Elizabeth A. Levy--.

Signed and Sealed this

Nineteenth Day of May, 1992

Attest:

DOUGLAS B. COMER

*Attesting Officer*     *Acting Commissioner of Patents and Trademarks*